United States Patent
Jain

Patent Number: 5,207,703
Date of Patent: May 4, 1993

[54] SUTURE ORGANIZER

[76] Inventor: Krishna M. Jain, 8405 Plover, Kalamazoo, Mich. 49002

[21] Appl. No.: 616,900

[22] Filed: Nov. 21, 1990

Related U.S. Application Data

[63] Continuation-in-part of Ser. No. 424,620, Oct. 20, 1989, abandoned.

[51] Int. Cl.⁵ ............................................. A61B 17/04
[52] U.S. Cl. .................................... 606/232; 606/233
[58] Field of Search .................................. 606/148–150, 606/222, 228, 232, 233; 206/340–345, 63.3, 388, 495; 24/713.9, 714.4, 714.5, 130

[56] References Cited

U.S. PATENT DOCUMENTS

| | | | |
|---|---|---|---|
| 595,482 | 12/1897 | Kempshall | 24/714.4 X |
| 743,909 | 11/1903 | Mitchell | 24/714.5 |
| 822,060 | 5/1906 | Lawler | 206/388 |
| 963,899 | 7/1910 | Kistler . | |
| 972,620 | 10/1910 | Hennessey | 24/713.9 |
| 1,344,227 | 6/1920 | Hauman | 606/148 |
| 1,466,673 | 9/1923 | Solomon et al. | 24/713.9 X |
| 1,983,810 | 12/1934 | Rice | 24/713.9 |
| 2,692,599 | 10/1954 | Creelman . | |
| 3,388,790 | 6/1968 | Slomczewski . | |
| 3,515,129 | 6/1970 | Truhan . | |
| 3,633,582 | 1/1972 | Steinman | 128/334 R |
| 3,654,668 | 4/1972 | Appleton | 24/130 R X |
| 3,695,271 | 10/1972 | Chodorow . | |
| 3,819,039 | 6/1974 | Erickson | 206/388 |
| 3,826,253 | 7/1974 | Larsh et al. . | |
| 3,931,821 | 1/1976 | Kletschka et al. . | |
| 3,951,261 | 4/1976 | Mandel et al. | 206/227 |
| 4,185,636 | 1/1980 | Gabbay et al. | 606/148 |
| 4,284,194 | 8/1981 | Flatau | 206/63.3 |
| 4,421,231 | 12/1983 | McCarn | 206/388 |
| 4,450,845 | 5/1984 | Engel | 128/743 |
| 4,492,229 | 1/1985 | Grunwald | 606/148 |
| 4,699,271 | 10/1987 | Lincoln et al. | 206/63.3 |
| 4,730,725 | 3/1988 | Marshall et al. | 206/63.3 |

FOREIGN PATENT DOCUMENTS 2114894  9/1983  United Kingdom ............... 606/148

*Primary Examiner*—Robert A. Hafer
*Assistant Examiner*—Brian E. Hanlon
*Attorney, Agent, or Firm*—Varnum, Riddering, Schmidt & Howlett

[57] ABSTRACT

A suture organizer 10 comprises a flat, platelike member 24 having a rank of fingerlike projections 28 extending from an upper surface 27 thereof. A layer of adhesive 32 is provided on a lower surface 30 of the platelike member 24 in order to adhere to a surgical drape 16 or sheet near the vicinity of a surgical incision 20. Sutures 18 are received in valleys 29 defined by the projections 28 thereby minimizing entanglement of the sutures after surgical attachment but prior to tying and cutting.

13 Claims, 3 Drawing Sheets

SUTURE ORGANIZER

CROSS-REFERENCE

This application is a continuation-in-part of U.S. patent application Ser. No. 07/424,620, filed Oct. 20, 1989 in the name of the present inventor, now pending.

BACKGROUND OF THE INVENTION

1. Field of the Invention

The invention relates generally to medical surgical accessories and, more particularly, to a lightweight organizer that may be readily secured to a sheet or surgical drape to efficiently retain and organize sutures during surgery.

2. Description of the Related Art

During surgery, a surgeon needs ready and efficient access to sutures. Traditional suture handling practice has been considered inefficient, clumsy and wasteful. Often sutures were laid out on towels and passed individually to the surgeon when needed. The sutures became entangled and difficult to separate; the suture supply was sometimes spilled or upset. As a result, a number of devices for dispensing packaged sutures have been developed. Examples of such devices are disclosed in U.S. Pat. No. 3,951,261 issued Apr. 20, 1976 to Mandel et al.; U.S. Pat. No. 4,284,194 issued Aug. 18, 1981 to Flatau; and U.S. Pat. No. 4,699,271 issued Oct. 13, 1987 to Lincoln et al.

Related devices which lay out and retain sutures in a neat and organized fashion before they are needed have been developed. These devices enable the surgical scrub nurse to deftly grasp an individual suture and pass it to the surgeon. However, the surgeon typically attaches numerous sutures to the patient before tying or knotting and cutting the individual sutures. The sutures are typically extended away from the surgical field and laid out on the surgical drape, the sutures being somewhat immobilized by a surgical clamp which is secured to the free end of each suture. Some operations such as vascular surgery require numerous fine sutures which can easily soon crowd the surgical field and become entangled before the surgeon can tie them. Untangling the sutures delays completion of the surgery and increases the trauma of the patient.

Thus there is a need for a device that will neatly and efficiently organize and retain sutures during surgery. Examples of such devices are disclosed in U.S. Pat. No. 4,185,636 to Gabbay et al. and U.S. Pat. No. 3,515,129 to Truhan. In the Gabbay et al. device, each suture is frictionally retained by a foam insert in a leg. In the Truhan device, the sutures are retained by wings. It takes considerable manipulation to place the suture in the retaining legs of the Gabbay et al. device, and there is nothing to prevent the sutures from becoming dislodged in the Truhan device. As well, these and similar devices have proven expensive to manufacture and include features which may damage delicate sutures.

SUMMARY OF THE INVENTION

In accordance with the invention, a suture organizer is provided for facilitating the orderly retention of sutures extending from an incision in a patient during surgery. The suture organizer comprises a base member with a substantially planar surface defined by an edge and a plurality of spaced-apart retaining members integrally formed with the base member and defining a plurality of spatial areas between the retaining members. The retaining members each comprise a stem portion extending normally from the planar surface and disposed away from said edge and a cap portion at one end of the stem portion. The cap portion has a laterally extending shoulder and the cap on adjacent stems define a restricted entrance to a spatial area defined between the adjacent stems and the shoulders tend to prevent unintentional removal of the sutures from the spatial areas. The stem and cap portions have rounded corners and the entire surface of the stem and cap portions are smooth and substantially free of discontinuities. Each spacial area can loosely retain a suture so that the organizer can be moved relative to the suture and the suture can be removed from the spacial area without causing damage to the suture. The shoulders further tend to prevent unintentional removal of the sutures from the spacial areas.

Preferably, the cap portions each comprise a convex, curved upper surface to define sloping entry walls for the restricted entrances. Conversely, the shoulders of the cap members comprise a substantially flat undersurface.

The end retaining members near opposite ends of the organizer each have an upwardly extending stem portion and a cap portion on one end of the step portion, but the cap portion has a laterally extending shoulder extending in only one direction from the stem portion.

In one aspect of the invention, the base member comprises opposite slotted openings near opposite ends of the base member to facilitate attachment of the suture organizer to a surface proximate to the incision.

In another aspect of the invention, the suture organizer comprises a one-piece body having a substantially planar base portion with an upper surface having an edge. A rank of protuberances extend normally from the upper surface and are spaced away from the edge of the base portion. The rank defines a plurality of spacial areas between adjacent protuberances with each protuberance having a distal end. The upper surface, the entire surface of each protuberance, the distal end of each protuberance and the junction between each protuberance and the upper surface are smooth and free of discontinuities so that the spacial areas can loosely retain a weighted suture providing for movement of the organizer relative to the suture without damaging the suture.

BRIEF DESCRIPTION OF THE DRAWINGS

The invention will now be described with reference to the drawings in which.

DETAILED DESCRIPTION OF THE PREFERRED EMBODIMENTS

Figure 1:
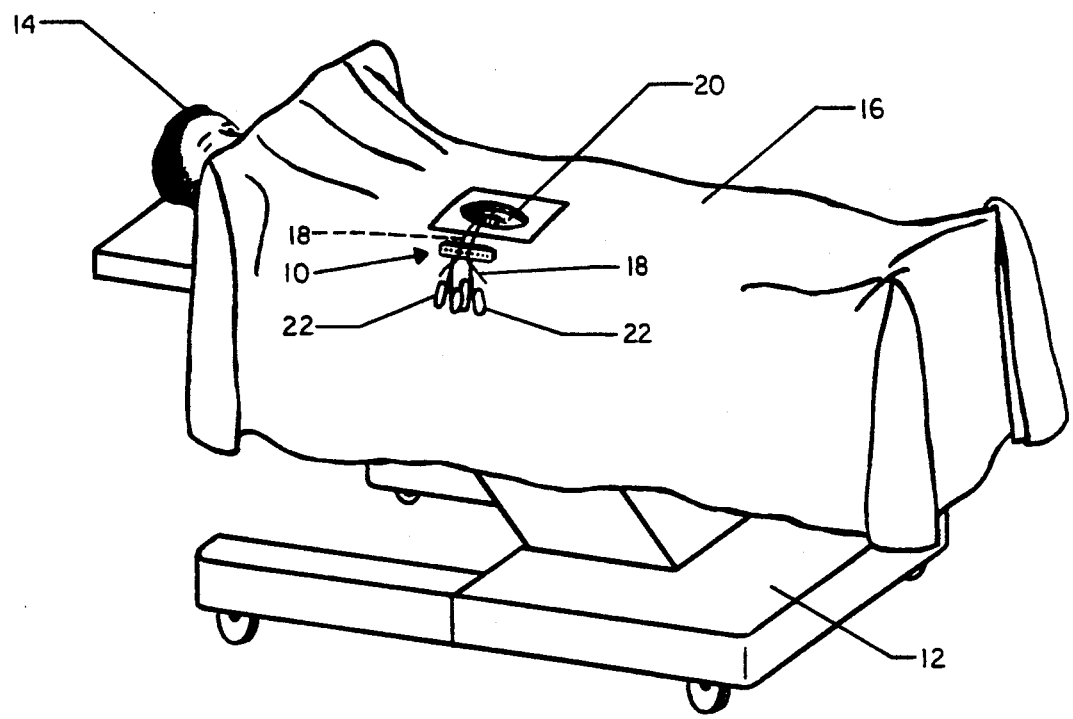
FIG. 1 is a perspective view showing a typical surgical procedure including an operating table, a patient protected by a surgical drape to provide a surgical field, and a suture organizer according to the invention secured to the surgical drape.
Figure 2:
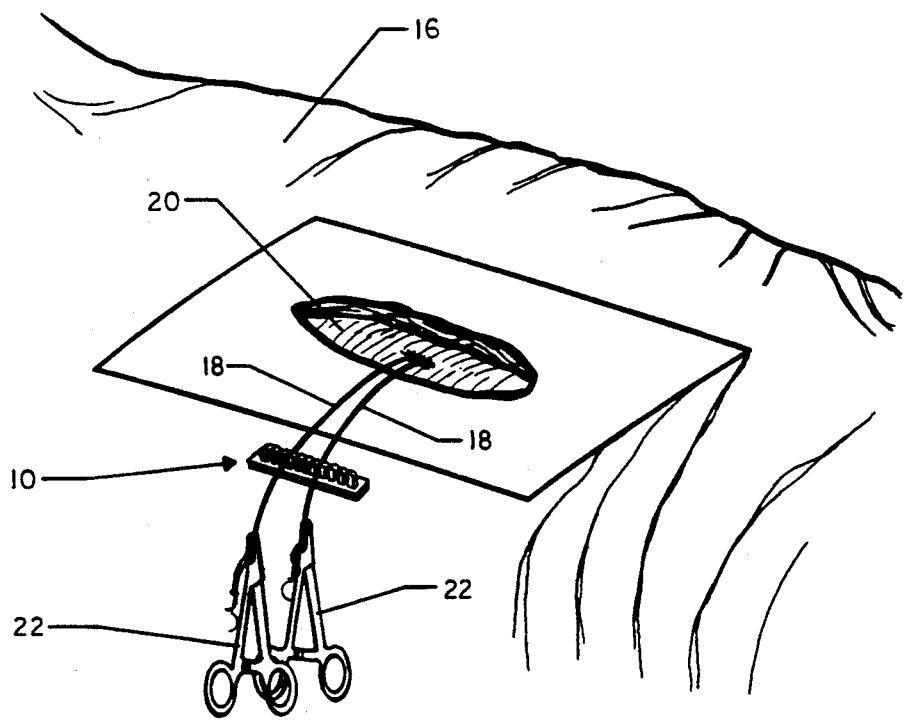
FIG. 2 is an enlarged perspective view similar to FIG. 1 showing the surgical field and the suture organizer with a plurality of sutures retained thereby.

Turning now to the drawings, and in particular FIGS. 1 and 2, a suture organizer 10 is shown in conjunction with an operating table 12 and a patient 14 thereon. The patient 14 is protected by a surgical drape 16 which defines a sterile surgical field. The suture organizer 10 is adapted to be secured to the surgical drape 16 in a manner described hereinbelow. Although only one suture organizer 10 is shown, several organizers may be used simultaneously and distributed about the surgical field in any arrangement that is convenient, the number and position of the organizers being determined by the needs of the particular surgery. A plurality of sutures 18 can be seen extending outwardly from an incision area 20, the sutures having already been attached to the patient 14 by the surgeon (not shown separately in the drawings) but not yet tied and cut. The sutures 18 engage and are retained by the suture organizer 10. The sutures 18 extend away from the suture organizer 10 and are further stabilized by surgical clamps 22 which rest on the surgical drape 16, one clamp being tightly secured to the free end of each suture.

Figure 3:
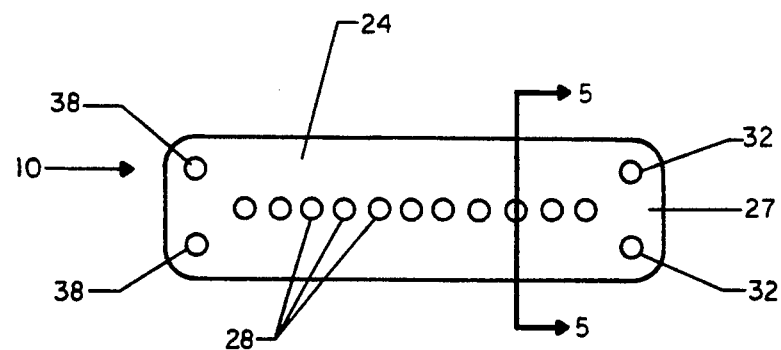
FIG. 3 is a top plan view of the suture organizer.
Figure 4:
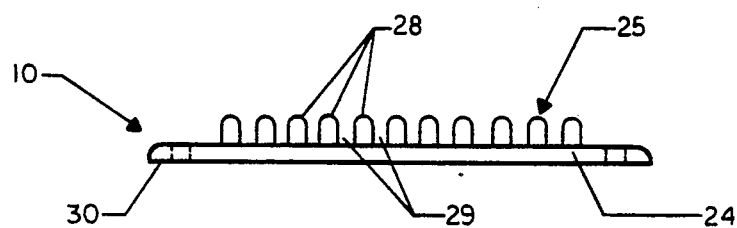
FIG. 4 is an elevational view of the suture organizer.
Figure 5:
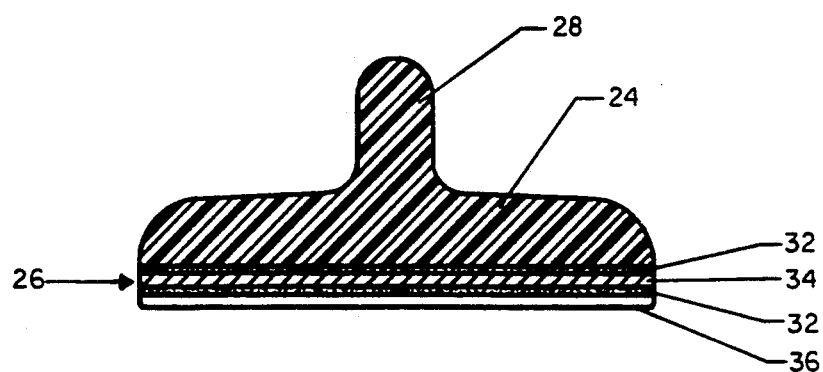
FIG. 5 is an enlarged sectional view taken along lines 5—5 of FIG. 3.

Referring now to FIGS. 3 to 5, the suture organizer 10 comprises a flat, platelike member 24 having retaining means 25 formed thereon for organizing the sutures 18 and securing means 26 for securing the suture organizer 10 to the surgical drape 16 or other adjoining material such as a sheet. The material from which the surgical drape 16 or the sheet is formed is not important so long as the material is adaptable for use with the securing means 26 to secure the organizer thereto. The platelike member 24 is of generally rectangular shape, although shape is not critical to the invention. The member 24 is preferably relatively small and lightweight so as not to interfere with the surgical procedure. The platelike member 24 may be inexpensively formed of any lightweight sterilizable material such as acrylonitrile-butadiene-styrene (ABS) plastic. If desired, the plastic can be made radio-opaque through the addition of a suitable filler such as barium sulfate. Thus, if the suture organizer 10 were to be inadvertently misplaced in the patient 14, it could be subsequently identified by a conventional X-ray procedure.

An upper surface 27 of the platelike member 24 is provided with a rank of fingerlike projections 28. Interstices valleys 29 between the projections are adapted to receive sutures 18, one per valley, and thus function to retain and organize the sutures 18 in an orderly fashion. The number of projections 28 is immaterial so long as there are at least two, thereby providing a single interstice or valley 29 therebetween. The projections 28 should be sufficiently spaced apart so that the sutures 18 do not become entangled. A valley width on the order of approximately 0.075" has been found useful. Preferably, the projections and valleys are constructed to provide a continuous, uninterrupted surface without sharp corners and edges. Thus constructed, delicate sutures are less likely to wear or break and will be easier to emplace and retrieve from the organizer.

A lower surface 30 of the platelike member 24 is provided with means 26 for securing the organizer 10 to the surgical drape 16 or any other sheet commonly associated with surgery, which means is shown in the form of a layer of adhesive 32. The adhesive 32 may be a medical grade adhesive, that is, an adhesive which is hypoallergenic, radiation tolerant, and capable of being sterilized. Examples of suitable materials are two acrylate adhesives, T-193 and T-694, presently marketed by the 3M Company, St. Paul, Minn. Alternatively, and preferably, the adhesive layer 32 may be provided by a layer of double-sided tape or the like in which event the adhesive layer would comprise a pair of discrete adhesive layers with an intermediate layer 34, such as polyethylene film sandwiched therebetween, as shown in FIG. 5. In this embodiment, it is not required that the adhesive layer 32 be a so-called medical grade adhesive. In a third embodiment, a layer of adhesive may be applied directly to the lower face of the base member 24. The adhesive layer 32 in any of the foregoing embodiments may be protected by a peel-away strip or layer of nonadhesive protective paper 36, the layer 36 being readily removable to expose the adhesive layer 32 for use. Such an arrangement is well known. In addition to or in place of the adhesive layer 32, the suture organizer 10 may be provided with apertures 38, which can be used to suture the organizer to the surgical drape 16 or sheet.

In a typical application, it is expected that the suture organizer 10 will be sufficiently economical to be disposed of after a single use. Thus, each suture organizer 10 will likely be provided with its own sterile package (not shown separately in the drawings) which can be opened by the surgical scrub nurse at the appropriate time. The organizer 10 will be removed from the package and the protective paper layer 36 peeled away to expose the adhesive layer 32. One or more suture organizers may then be distributed about the surgical field by securing the organizer 10 to the surgical drape 16 or sheet with the adhesive layer 32. (Alternatively, the organizer may be sutured to the drape 16 or sheet by way of the apertures 38). As noted above, the number and placement of the suture organizers will be dictated by the requirements of the surgical procedure. It is expected that the organizers 10 will be positioned relatively close to the incision area 20.

Once the surgeon has attached a suture 18 to the patient 14, the suture with its associated surgical clamp 22 secured thereto is extended away from the incision area 20. The suture is received within the valley 29 between two adjacent projections 28. The end of the suture 18 having the clamp 22 attached thereto is allowed to rest more or less freely, the weight provided by the clamp 22 in cooperation with the organizer 10 being sufficient to tension the suture 18 and prevent it from becoming entangled with adjacent sutures that are similarly retained in adjacent valleys 29.

Figure 6:
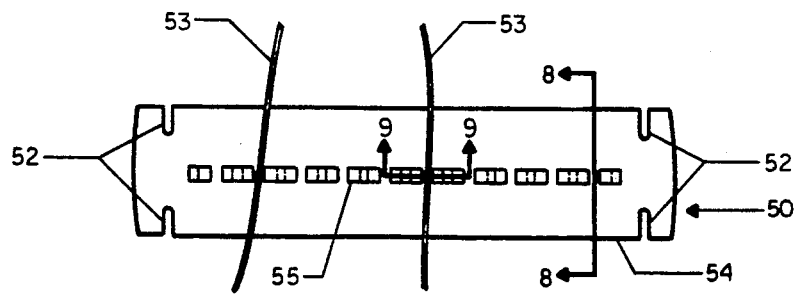
FIG. 6 is a plan view of an alternate embodiment of a suture organizer in accordance with the present invention.

Referring to FIG. 6, there is shown a suture organizer 50 comprising a flat platelike member 54 having a plurality of spaced-apart, linearly aligned, suture-retaining members 55 formed on the plate member 54. Retaining members 55 are formed to define spatial areas 59 for readily accepting sutures or the like and are designed to minimize unintentional release of the sutures. The plate member 54 may be provided with an adhesive tape (not shown in the drawing) on its underside to allow the suture organizer 50 to be attached to a surgical drape such as surgical drape 16, or the like. Alternatively, the suture organizer may be sewn or otherwise attached to a surgical drape by guiding a common sewing thread or the like in slotted openings 52 provided for that purpose. A plurality of sutures 53 may be retained in the several spatial areas defined between the plurality of retaining members 55, as depicted, for example, in FIGS. 1 and 2. It will be appreciated that the number of retaining members 55 incorporated in the suture organizer 50 will depend on the length of the plate member 54 and is a matter of design preference.

Figure 7:
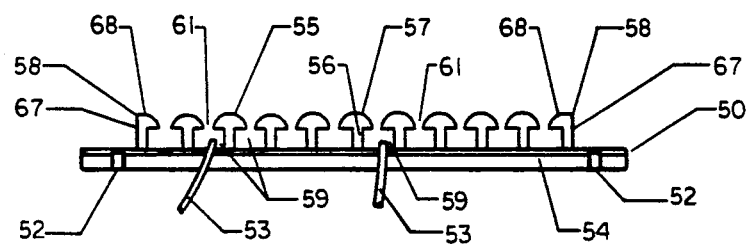
FIG. 7 is an elevational view of the suture organizer of FIG. 6.

FIG. 7 is an elevational view of the suture organizer 50 and shows a plurality of spatial areas 59 defined between adjacent retaining members 55. The inner spatial areas 59 are formed with sides defined by stem portions 56 of the retaining members 55. The spatial areas have a relatively narrow entrance 61 defined by cap portions 57 of adjacent retaining members 55. The suture organizer 50, comprising plate member 54 and retaining members 55 formed integral with the plate member, may be inexpensively formed from any appropriate material for such purposes, such as the well-known acrylonitrile-butadiene-styrene (ABS) plastic.

Figure 9:
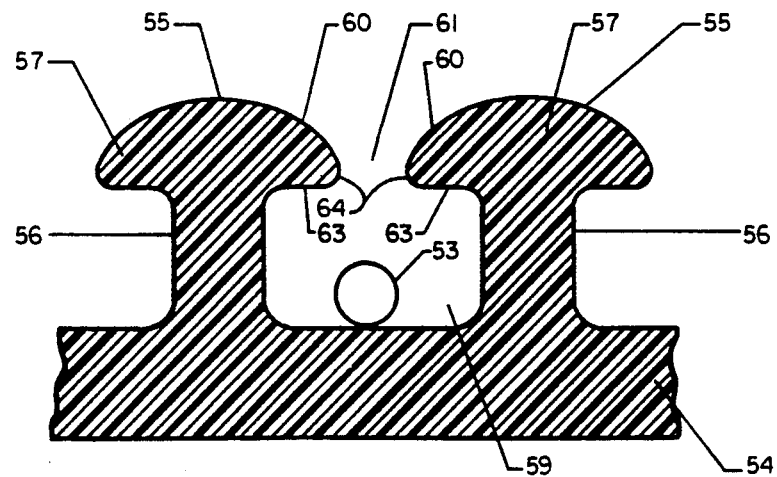
FIG. 9 is an enlarged fragmentary sectional view taken along line 9—9 of FIG. 6.

The retaining members 55 are shown in greater detail in FIG. 9, which is an enlarged fragmentary sectional view along line 9—9 of FIG. 6. Each set of two adjacent suture-retaining members 55 define space between them for retaining a suture, such as sutures 53 illustratively shown in the drawing. Each of the retaining members 55 is provided with an upwardly extending stem portion 56 and a cap portion 57 attached to the stem portion 56. The stem portions 56 of adjacent retaining members are spaced apart by a selected distance, e.g., on the order of 0.25 inches, and each stem is of a selected width, e.g., on the order of 0.08 inches. In this manner, adjacent stem members are used to define a spatial area in which a standard surgical suture is loosely retained. Cap members 57 are each provided with a convex curved surface 60 to define sloping entry walls at the entrance 61 to the spatial area 59, thereby facilitating entry of a suture. The cap members 57 are each provided with a substantially flat laterally extending undersurface or shoulder 63. The shoulders 63 tend to prevent unintentional or accidental removal of a suture, such as suture 53, from spatial area 59. Shoulders 63 are provided with rounded edges 64 to facilitate the intentional removal of a suture from the spatial area 59 and to avoid damaging a suture during removal. By way of example, cap portions 57 may be of a selected width such that the narrowest part of opening 61 has a width of approximately 0.06 inches. Using such dimensions, the fine surgical sutures may be readily inserted and removed while providing a means for safely retaining the sutures.

Figure 8:
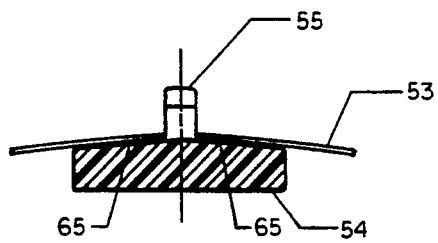
FIG. 8 is a sectional view taken along line 8—8 of FIG. 6.

As shown in FIG. 7, the suture organizer 50 may be conveniently provided with end retaining members 58, each of which is provided with a partial cap portion 68 cooperating with adjacent retaining members 55 to safely retain sutures. The external sides 67 of the end retaining members 58 are essentially smooth to avoid unnecessary snagging or catching of the sutures or other materials on the end members. FIG. 8 is a sectional view along line 8—8 of FIG. 6 showing plate member 54 in cross section and showing an end view of one of the retaining members 55. Plate member 54 is provided with an upper surface 65 having a gentle slope away from the centerline of the plate member 54. In one exemplary embodiment, the thickness of the plate member at the outer side edges is on the order of 0.15 inches, and the slope toward the side edges is on the order of five degrees.

Thus it can be seen that an efficient, economical, lightweight means for organizing sutures prior to their knotting or tying and cutting has been provided.

Reasonable variations or modifications are possible within the spirit of the foregoing specification and drawings without departing from the scope of the invention which is defined in the accompanying claims.

I claim:

1. A suture organizer for facilitating the orderly retention of sutures extending from an incision in a patient during surgery, said organizer comprising:

a base member having a substantially planar surface defined by an edge;

a plurality of spaced-apart retaining members integrally formed with said base member and defining a plurality of spatial areas between adjacent retaining members, said retaining members each comprising a stem portion extending normally from said planar surface and disposed away from said edge and a cap portion at one end of said stem portion, said cap portion having a laterally extending shoulder, wherein cap portions on adjacent stems define a restricted entrance to a spatial area defined between adjacent stems; and rounded corners on said stem portions and said cap portions, the entire surface of said stem portions and said cap portions being smooth and substantially free of discontinuities whereby each spatial area provides for loosely retaining a suture therein so that the organizer can be moved relative to the suture without damaging the suture, and the suture can be removed from the spatial area without damage, and said shoulders tend to prevent unintentional removal of said sutures from said spatial areas.

2. The suture organizer in accordance with claim 1 wherein said cap portions each comprise a convex curved upper surface, to define sloping entry walls for said restricted entrances, whereby entry of said sutures into said spatial areas is facilitated.

3. The suture organizer in accordance with claim 2 wherein said shoulders of each of said cap members each comprise a substantially flat undersurface of said cap members.

4. The suture organizer in accordance with claim 1 wherein said suture organizer comprises a pair of end retaining members near opposite ends of said organizer, each of said end retaining members having a normally extending stem portion and a cap portion on one end of said stem portion, said cap portion having a laterally extending shoulder extending in one direction only from said stem portion of said end retaining members.

5. The suture organizer in accordance with claim 4 wherein said base member comprises opposing slotted openings near opposite ends of said base member to facilitate attachment of said suture organizer to a surface proximate to the incision.

6. The suture organizer in accordance with claim 5 wherein said base member has an upper surface and a centerline and said upper surface comprises surface areas extending downwardly and away from said centerline.

7. A suture organizer for facilitating the orderly retention of sutures extending from a patient during surgery, said organizer comprising:

a one-piece body having a substantially planar base portion with an upper surface having an edge and a rank of protuberances extending normally from the upper surface and spaced away from said edge, said rank defining a plurality of spatial areas between adjacent protuberances, each protuberance having a distal end, wherein the upper surface and the entire surface of each protuberance, each distal end of each protuberance and the junction between each protuberance and the upper surface is smooth and free of discontinuities, whereby the spatial areas provide for loosely retaining a weighted suture in one of the spatial areas so that the organizer can be moved relative to the suture without damaging the suture.

8. A suture organizer according to claim 7 wherein each distal end has a laterally extending shoulder so that shoulders on adjacent protuberances define a restricted entrance to each one of the spatial areas.

9. A suture organizer according to claim 8 wherein the distal ends each have a rounded surface to define sloping entry walls for the restricted entrances.

10. A suture organizer according to claim 9 further comprising opposed slotted openings near opposite ends of the base portion to facilitate attachment of the body to a surface proximate an incision.

11. A suture organizer according to claim 9 wherein the base portion has a lower surface opposite the upper surface and a layer of adhesive is disposed on the lower surface to facilitate attachment of the body to a surface proximate the incision.

12. A suture organizer according to claim 7 further comprising opposed slotted openings near opposite ends of the base portion to facilitate attachment of the body to a surface proximate an incision.

13. A suture organizer according to claim 7 wherein the base portion has a lower surface opposite the upper surface and a layer of adhesive is disposed on the lower surface to facilitate attachment of the body to a surface proximate the incision.

* * * * *